US008923584B2

(12) United States Patent
Chabanas et al.

(10) Patent No.: US 8,923,584 B2
(45) Date of Patent: Dec. 30, 2014

(54) METHOD AND SYSTEM OF AUTOMATIC DETERMINATION OF GEOMETRIC ELEMENTS CHARACTERIZING A BONE DEFORMATION FROM 3D IMAGE

(75) Inventors: Laurence Chabanas, Saint-Pierre-d'Allevard (FR); Stéphane Lavallee, Saint-Martin-d'Uriage (FR); Jerome Tonetti, Grenoble (FR); Thomas Byrd, Nashville, TN (US); Bryan Talmadge Kelly, Riverside, CT (US); Christopher Larson, Edina, MN (US)

(73) Assignee: A2 Surgical, Saint-Pierre-d'Allevard (FR)

( * ) Notice: Subject to any disclaimer, the term of this patent is extended or adjusted under 35 U.S.C. 154(b) by 75 days.

(21) Appl. No.: 13/704,218

(22) PCT Filed: Jun. 16, 2011

(86) PCT No.: PCT/IB2011/001687
§ 371 (c)(1),
(2), (4) Date: Dec. 13, 2012

(87) PCT Pub. No.: WO2011/158117
PCT Pub. Date: Dec. 22, 2011

(65) Prior Publication Data
US 2013/0083984 A1    Apr. 4, 2013

Related U.S. Application Data

(60) Provisional application No. 61/355,206, filed on Jun. 16, 2010.

(51) Int. Cl.
*G06K 9/00*    (2006.01)
*G06T 7/60*    (2006.01)
(Continued)

(52) U.S. Cl.
CPC ......... *G06T 7/0012* (2013.01); *G06T 2219/012* (2013.01); *G06T 7/604* (2013.01);
(Continued)

(58) Field of Classification Search
USPC .................. 382/128, 131, 154; 128/922, 923
See application file for complete search history.

(56) References Cited

U.S. PATENT DOCUMENTS 5,995,738 A    11/1999  DiGioia et al.
6,750,974 B2 *  6/2004  Svetkoff et al. ............... 356/602
(Continued)

FOREIGN PATENT DOCUMENTS

JP    2009273521    11/2009

OTHER PUBLICATIONS

Dudda M. et al, "Do Normal Radiographs Exclude Asphericity of the Femoral Head-Neck Junction?", Clin Orthop Relat Res (2009) 467:651-659.

(Continued)

*Primary Examiner* — Yosef Kassa
(74) *Attorney, Agent, or Firm* — David L. Fox, The JL Salazar Law Firm

(57) ABSTRACT

The invention relates to a method for automatically determining, on a bone comprising a head portion contiguous to a neck portion, parameters for characterizing a bump deformation on the head-neck junction of the bone from acquired 3D medical image, the method comprising the following steps: i) constructing a 3D surface model of the bone; ii) fitting a sphere on the spherical portion of the head of the bone; iii) determining a neck axis characterizing the neck portion of the bone; iv) determining from the fitted sphere and the neck axis, a clock face referential on the head of the bone rotating around the neck axis; v) determining a 3D curve on the 3D surface model characterizing the head-neck junction of the bone; vi) determining, from the 3D curve, the summit of the bump deformation of the head-neck junction of the bone; vii) determining, from said summit of the bump deformation, first and a second parameters (α3D, iMax) characterizing the maximum bump deformation of the head-neck junction of the bone.

12 Claims, 9 Drawing Sheets

(51) Int. Cl.
  *G06T 19/00* (2011.01)
  *G06T 7/00* (2006.01)
  *G06T 17/00* (2006.01)
  *A61B 19/00* (2006.01)

(52) U.S. Cl.
  CPC ..... *A61B 2019/505* (2013.01); *G06T 2207/10072* (2013.01); *A61B 2019/461* (2013.01); *G06T 2207/30008* (2013.01); *G06T 19/00* (2013.01); *G06T 17/00* (2013.01); *Y10S 128/922* (2013.01); *Y10S 128/923* (2013.01)
  USPC ........... 382/128; 382/131; 382/154; 128/922; 128/923

(56) References Cited

U.S. PATENT DOCUMENTS

| | | | | |
|---|---|---|---|---|
| 7,184,814 | B2* | 2/2007 | Lang et al. | 600/416 |
| 7,199,882 | B2* | 4/2007 | Svetkoff et al. | 356/602 |
| 7,519,209 | B2* | 4/2009 | Dawant et al. | 382/128 |
| 7,672,709 | B2 | 3/2010 | Lavallee et al. | |
| 7,953,204 | B2* | 5/2011 | Sumanaweera et al. | 378/65 |
| 8,358,818 | B2* | 1/2013 | Miga et al. | 382/128 |
| 8,395,620 | B2* | 3/2013 | El Dokor et al. | 345/424 |
| 8,405,656 | B2* | 3/2013 | El Dokor et al. | 345/422 |
| 8,437,521 | B2* | 5/2013 | Lu et al. | 382/128 |
| 8,488,863 | B2* | 7/2013 | Boucheron | 382/133 |
| 8,768,022 | B2* | 7/2014 | Miga et al. | 382/128 |
| 2005/0143676 | A1 | 6/2005 | De Guise et al. | |
| 2007/0122233 | A1 | 5/2007 | Maier et al. | |
| 2007/0195933 | A1 | 8/2007 | Bogojevic et al. | |
| 2007/0249967 | A1 | 10/2007 | Buly et al. | |
| 2008/0086150 | A1 | 4/2008 | Mathis et al. | |
| 2008/0177173 | A1 | 7/2008 | Deffenbaugh et al. | |
| 2008/0214960 | A1 | 9/2008 | Hodgson et al. | |
| 2008/0312663 | A1 | 12/2008 | Haimerl et al. | |
| 2008/0319449 | A1 | 12/2008 | Tuma et al. | |
| 2009/0017430 | A1 | 1/2009 | Muller-Daniels et al. | |
| 2009/0089034 | A1 | 4/2009 | Penney et al. | |
| 2009/0112214 | A1 | 4/2009 | Philippon et al. | |
| 2009/0285465 | A1 | 11/2009 | Haimerl et al. | |
| 2010/0049493 | A1 | 2/2010 | Haimerl | |

OTHER PUBLICATIONS

Rakhra K.S. et al, "Comparison of MRI Alpha Angle Measurement Planes in Femoroacetabular Impingement", Clin Orthop Relat Res (2009) 467:660-665.
Kang et al, "Accurate simulation of hip joint range of motion", Computer Animation Conference—CA, pp. 215-219, 2002.
Brunner A. et al., "Evaluation of a Computed Tomography—Based Navigation System Prototype for Hip Arthroscopy in the Treatment of Femoroacetabular Cam Impingement", Arthroscopy: The Journal of Arthroscopic and Related Surgery, vol. 25, No. 4 Apr. 2009: pp. 382-391.
Arbabi E. et al, "A fast method for finding maximum range of motion in the hip joint", CAOS 2007, Heidelberg, Germany, p. 20-23.
Arbabi E. et al, "Penetration Depth Method—Novel Real-Time Strategy for Evaluating Femoroacetabular Impingement", Journal of Orthopaedic Research, vol. 28, Issue 7, pp. 880-886, Jul. 2010.
Dario P. et al, "A Novel Mechatronic Tool for Computer-Assisted Arthroscopy", IEEE Engineering in Medicine and Biology Society 2000;4(1):15-29.
Hodgson A.J. et al, "Computer-assisted femoral head resurfacing", Computer Aided Surgery, Sep./Nov. 2005; 10(5/6): 337-343.
Kendoff D. et al, "Feasibility of a navigated registration technique in FAI surgery", Archives of Orthopaedic and Trauma Surgery, vol. 131, No. 2, pp. 167-172, 2011.
Wengert C. et al, "Markerless Endoscopic Registration and Referencing", Med Image Comput Comput Assist Interv. 2006;9(Pt 1):816-23.
Monahan E. et al, "Computer-aided navigation for arthroscopic hip surgery using encoder linkages for position tracking", Int J Med Robotics Comput Assist Surg 2006; 2: 271-278.
Monahan E. et al, "A study of user performance employing a computer-aided navigation system for arthroscopic hip surgery", Int J CARS (2007) 2:245-252.
Charbonnier C. et al, "Motion study of the hip joint in extreme postures", The Visual Computer, vol. 25, No. 9, pp. 873-882, 2009.
Gilles B. et al, "MRI-based Assessment of Hip Joint Translations", J Biomech, vol. 42, Jun. 2009.
Murphy S.B. et al, "Arthroscopic percutaneous computer assisted FAI relief using a new method of CT-fluoro registration", Computer-Assisted Orthopedic Surgery-International, 2007.
Barrett A.R.W et al, "Preoperative planning and intraoperative guidance for accurate computer-assisted minimally invasive hip resurfacing surgery", Proc. IMechE vol. 220 Part H, 2006.
Puls M. et al, "Simulation of Hip Motion for Impingement Detection: A Comparison of Four Strategies", Journal of Biomechanics 41(S1), 16th ESB Congress, Oral Presentations, Tuesday Jul. 8, 2008.
Cai D. et al, "Rapid Impingement Detection System with Uniform Sampling for Ball-and-Socket Joint", Workshop on 3D Physiological Human, Zermatt, Switzerland, Dec. 1-4, 2008.
Tannast M. et al, <<Computer-assisted Simulation of Femoroacetabular Impingement Surgery >>, In JB Stiehl, WH Konermann, RG Haaker, AM DiGioia (eds.): "Navigation and MIS in Orthopaedic Surgery", Berlin, Heidelberg, New York: Springer-Verlag. pp. 448-455, 2006.
Tannast M. et al, "Noninvasive three-dimensional assessment of femoroacetabular impingement", Journal of Orthopedic Research, Jan. 2007.
Wu C., "3D Reconstruction and Tracking of Anatomical Structures from Endoscopic Images", Thesis, 2009.
Charbonnier C. et al, "Virtual Hip Joint: from Computer Graphics to Computer-Assisted Diagnosis", Eurographics 2009, Mar. 30-Apr. 3, Munich, Germany.
Zaragoza E.J., "3D CT and the Imaging Approach to Femoroacetabular Impingement Syndrome", Section 4, Orthopedic Imaging, TeraRecon Clinical Case Studies—vol. 1, pp. 143-150.
Nötzli et al, "The Contour of the Femoral Head-Neck Junction as a Predictor for the Risk of Anterior Impingement," Journal of Bone and Joint Surgery (BR), vol. 84-B, No. 4, May 2002, pp. 556-560.
Ito et al, "Femoroacetabular Impingement and the Cam-Effect," Journal of Bone and Joint Surgery [BR], vol. 83-B, No. 2, Mar. 2001, pp. 171-176.
Pfirrmann Christian W.A. et al, "Cam and Pincer Femoroactabular Impingement : Characteristic MR Arthrographic Findings in 50 Patients", Radiology, Sep. 2006 LNKD—Pubmed 16857978, vol. 240, n° 3, Sep. 2006 (2006-2009), pp. 778-785, XP002665712.
Meyer Dominik C et al, "Comparison of six radiographic projections to assess femoral head/neck asphericity", Clinical orthopaedics and related research Apr. 2006, LNKD, Pubmed 16456309, vol. 445, Apr. 2006, pp. 181-185, XP002665713.
Hossain M et al., "Current Management of femoro-acetabular impingement", Current Orthopaedics, Churchill Livingstone, vol. 22, n° 4, Aug. 1, 2008, pp. 300-310, XP025404285.
Miese Falk R et al. <<MRI morphometry, cartilage damage and impaired function in the ollow-up after slipped capital femoral epiphysis >>, Skeletal Radiology, Jun. 2010 LNKD-Pubmed 20177672, vol. 39, n° 6, Feb. 24, 2010, pp. 533-541, XP002665714.
Jun Y et al :"design of patient-specific hip implants based on the ZD geometry of the human femur", Advances in engineering software, Elsevier Science, Oxford, GB, vol. 41, n° 4, Apr. 1, 2010, pp. 537-547, XP026903755.
Logishetty K et al., "The role of navigation and robotic surgery in hip arthroscopy", operative techniques in orthopaedics, Saunders, Philadelphia, PA, US, vol. 20 n° 4, Dec. 1, 2010, pp. 255-263, XP02755637.
International Search Report for International Application No. PCT/182011/001687, mailed Dec. 29, 2011.
Examination Report for European Patent Application No. 11768077.7 dated Dec. 12, 2013, 7 pages.
Patent Examination Report No. 1 for Australian Patent Application No. 2011266700 dated Apr. 30, 2014, 4 pages.

* cited by examiner

US 8,923,584 B2

METHOD AND SYSTEM OF AUTOMATIC DETERMINATION OF GEOMETRIC ELEMENTS CHARACTERIZING A BONE DEFORMATION FROM 3D IMAGE

TECHNICAL FIELD

The invention relates to the field of computer assisted surgical planning, and more particularly to a method and a system for the characterization of a bone deformation from acquired 3D medical image.

BACKGROUND OF THE INVENTION

Articulations of the human body are often very complex systems and no precise generic model exists to capture all the variability from one articulation to another. It is therefore necessary to use specific medical images or collection of digital patient data in order to get relevant information to develop techniques, devices and methods that will facilitate a treatment or a diagnosis. The present text focuses on the hip articulation between the acetabulum and the proximal femur although it can be easily extended to other articulations such as shoulder for example.

Structural abnormalities in the morphology of the hip can limit motion and result in repetitive impact of the proximal femoral neck against the acetabular labrum and its adjacent cartilage. Femoro Acetabular Impingement (FAI) is a pathology that can result from a decreased femoral head-neck offset (cam effect), an overgrowth of the bony acetabulum (pincer effect), excessive acetabular retroversion or excessive femoral anteversion, or a combination of these deformities. The cam impingement is generally characterized by a bone overgrowth located at the antero-superior aspect of the femur head-neck junction, which destructures the spherical shape of the femur head. The pincer impingement is generally characterized by an overcoverage located at the anterior aspect of the acetabulum rim. However, the correct and full diagnosis of this pathology is not easy to determine, especially when dealing with subtle deformities.

Standard radiographic X-rays are used for the initial diagnosis and then three dimensional (3D) Computed Tomography (CT) scans or Magnetic Resonance Imaging (MRI) exams are generally performed in case of suspected FAI pathology. It is known in the clinical literature to produce reformatted slices from 3D medical image volume, to create two dimensional (2D) image slices in different orientation in order to increase the chance of detecting bone deformation.

Especially in cases of FAI, it is known to reconstruct a pseudo axial slice passing through the middle of the neck axis and to characterize the loss of sphericity of the femoral head by measuring an angle constructed from the neck axis and a radius of a circle fitted to the femoral head passing at the location where the bone surface quits the contour of the circle (definition of so-called "alpha angle" by Nötzli et al, in Journal of Bone and Joint Surgery, Volume 84-B, No. 4, May 2002, pages 556-560).

It is also known to create radial reformatted slices, by rotating the reformatting image plane along the neck axis at regular angular intervals, thus enabling the characterization of the bone deformation at several locations around the head-neck junction (Ito et al, in Journal of Bone and Joint Surgery [Br], Volume 83-B, No. 2, March 2001, pages 171-176).

Thus the alpha angle measurement as defined by Nötzli et al is also known to have been extended to a series of radial reformatted slices (Pfirrmann et al, in Radiology, Volume 240, No. 3, September 2006, pages 778-785).

Another important measurement is the orientation of the femoral neck, especially the version of the neck which is measured relatively to the knee rotation axis. This measurement is usually performed by measuring independently the orientation of the posterior condyles and the neck orientation in axial slices of the 3D image volume, and then recomputing from these two measures, a femoral neck version. The final neck version measurement thus being a combination of two measurements, only taking two dimensions into account, not reflecting true 3D orientation.

However, such processing of the 3D image remains a laborious manual task, comprising manual identification of the neck axis and manual fitting of a circle to the head of the bone in several 2D images, which cannot ensure accuracy and reproducibility, and can potentially mislead the diagnosis or the surgical indication.

The surgical treatment of FAI aiming at restoring a normal spherical shape to the femur head at the level of the bony cam lesion on the head neck-junction, it is crucial to have analysed and characterized as precisely as possible the location and the extent of the lesion. Moreover, as the surgeon will be addressing a 3D problem in the operating room, it is most important that the problem has been properly analysed in actual 3D and not only from sets of 2D slices.

From the issues described above, it can be easily understood that new specific methods are needed to answer the problems of bone deformation analysis.

The specific problem addressed by the invention is the difficulty to characterize precisely in three-dimensional space and in a fast and reproducible manner the bone deformation to be treated surgically, from pre-operative 3D image of the patient.

SUMMARY OF THE INVENTION

The invention provides a method for automatically determining, on a bone comprising a head portion contiguous to a neck portion, parameters for characterizing a bump deformation on the head-neck junction of the bone from acquired 3D medical image, the method comprising the following steps:
i) constructing a 3D surface model of the bone from acquired 3D medical image;
ii) fitting a sphere on the spherical portion of the head of the bone;
iii) determining a neck axis characterizing the neck portion of the bone;
iv) determining from the fitted sphere and the neck axis, a clock face referential on the head of the bone rotating around the neck axis;
v) determining a 3D curve on the 3D surface model characterizing the head-neck junction of the bone;
vi) determining, from the 3D curve, the summit of the bump deformation of the head-neck junction of the bone, said summit being the point on the 3D curve closest to the apex point of the head of the bone in the direction of the neck axis;
vii) determining, from said summit of the bump deformation, first and a second parameters ($\alpha 3D$, iMax) characterizing the maximum bump deformation of the head-neck junction of the bone, wherein the first parameter ($\alpha 3D$) is the angle between the hemi-line issued from the center of the fitted sphere in the neck axis direction and the segment joining the center of the fitted sphere and the summit of the bump deformation, and the second parameter (iMax) is a clock index locating on the clock face referential the summit of the bump deformation.

The step of determining the clock face referential is advantageously performed by an automatic computation comprising of the following steps:

i) determining a 12 o'clock superior coronal hemi-plane passing through the neck axis of the bone;
ii) determining on the head of the bone the 12 o'clock index at the location of the intersection of the coronal hemi-plane and the 3D surface model of the bone, at the most superior portion of the head of the bone;
iii) determining on the head of the bone the successive clock indices by rotating the coronal hemi-plane around the neck axis for each hour, the current hour index being determined at the location of the intersection of the current rotated hemi-plane and the 3D surface model of the bone.

Said 12 o'clock superior coronal hemi-plane may be determined from a superior portion of a coronal plane containing the neck axis and passing through a knee center point defined from the knee 3D image from and which with the the center of the fitted sphere determines the 3D mechanical vertical axis; the superior portion of the coronal plane being the hemi-plane starting at the level of the neck axis and extending in the opposite direction from the knee center point.

The step of determining the 3D curve may be performed by an automatic computation comprising the following steps:

i) determining a set of radial hemi-planes containing the neck axis and rotating around neck axis on the clock face referential;
ii) determining for each radial hemi-plane a point issued from the apex of the fitted sphere and moving in the direction of the neck along a head contour curve determined from the intersection of the 3D surface model and the radial hemi-plane;
iii) determining the first position of the point moving along the head contour curve where it is lying outside a circle determined by the intersection of the fitted sphere and the radial hemi-plane, over a predefined threshold distance from the contour of the circle; this point defining a head-neck junction limit point;
iv) determining from all radial hemi-planes a set of 3D head-neck junction limit points;
v) determining a 3D curve on the 3D surface model of the bone as an optimal 3D curve passing through the set of 3D intersecting points; the 3D curve defining the 3D head-neck junction curve.

The radial hemi-planes are preferably determined at regular angular intervals, at least for every hour around the clock face referential.

The predefined threshold is preferably in an interval of minimum 0.5 mm and maximum 2 mm.

The determination of a head-neck junction limit point in one radial hemi-plane may further comply with the condition that its neighbour points within a maximum distance of 2 mm further down along the head contour curve in the direction of the neck are also lying outside the circle over the threshold distance.

The determination of each head-neck junction limit point in all radial hemi-planes may further comprise an adjustment of their position within the threshold limit, along their respective head contour curve so to minimize the relative 3D distance of contiguous pairs of point in contiguous triplets of 3D head-neck junction limit points.

Said optimal curve is advantageously determined by a 3D pecked line joining contiguous points in the set of 3D head-neck junction limit points.

According to another embodiment, said optimal curve is determined by a 3D spline curve of minimal length interpolating the contiguous points in the set of 3D head-neck junction limit points.

The points in the set of 3D head-neck junction limit points may further be adjusted along their respective femoral head contours, while still lying outside the fitted sphere contour within the limit of the predefined threshold distance, so as to produce a smooth slope of the 3D head-junction curve at the location of each 3D head-neck junction limit point.

Another object of the invention is a system for determining, on a bone comprising a head portion contiguous to a neck portion, parameters for characterizing a bump deformation on the head-neck junction of the bone from acquired 3D medical image, the system comprising a computer including a memory and a processing unit adapted to run a computer program, wherein said computer program comprises at least one algorithm applying the method of one of claims 1 to 11.

DETAILED DESCRIPTION OF THE INVENTION:

Hereafter, description of the invention will be made with reference to the articulation of the hip. However, the invention is not limited to this illustrative example and the person skilled in the art will easily transpose this description to any other articulation partially formed by a bone head, such as the shoulder.

Some critical anatomical elements are necessary to measure some specific anatomical characteristics of the proximal femur, such as the femoral neck version angle, and the amplitude of the head-neck junction bump deformation measured by the alpha angle, which participates in the characterization of the proximal femur deformity in Femoro Acetabular Impingement (FAI) pathology.

The method is described by specifically addressing the femur but it can be extended to other bones of the human or animal body such as the humerus or other bones having a rotoid articulation. The general purpose of the invention is to determine from the 3D image of the bone, major parameters for characterizing a bump deformation on the head-neck junction of the bone, in a fast, precise and reproducible manner. The method detailed hereafter has to be understood as an algorithm implemented in the form of a software program on a processing unit.

The head of the bone is assumed to have a spherical portion and the neck is assumed to have roughly a diabolo shape. The deformation of the bone consists in the formation of a bump at the head neck junction, generally in a location where there are repetitive collisions between the femur and the acetabulum during hip motion. As described earlier, the characterization of the anatomy is based on the measurement of the neck version angle, and the characterization of the deformation is based on the measurement of the alpha angle, in one or several 2D slices in the 3D image volume.

In standard practice, the determination of those characteristic elements of a bone are performed manually by the radiologist in the 3D image, using interactive software tools that rely mostly on reformatted 2D images in the 3D image volume. Working on 2D images for determination of 3D geometric elements leads to errors. Interactive software using a mouse is also prone to human errors. And in all cases, such determination is time consuming.

In order to compute accurate characteristic anatomical values for the femoral bone features such as the neck version angle, and the alpha angle in three dimensions, the computations need to be based on the precise determination of the following reference anatomical elements: the femoral head sphere center and radius, the femoral neck axis, the clock face on the femoral head, and the knee rotation axis. The purpose of the invention is to describe a method of automatic and accurate determination of the characterization values of the femoral anatomy deformity very quickly, based on of those critical geometric elements from the 3D image.

Figure 1:
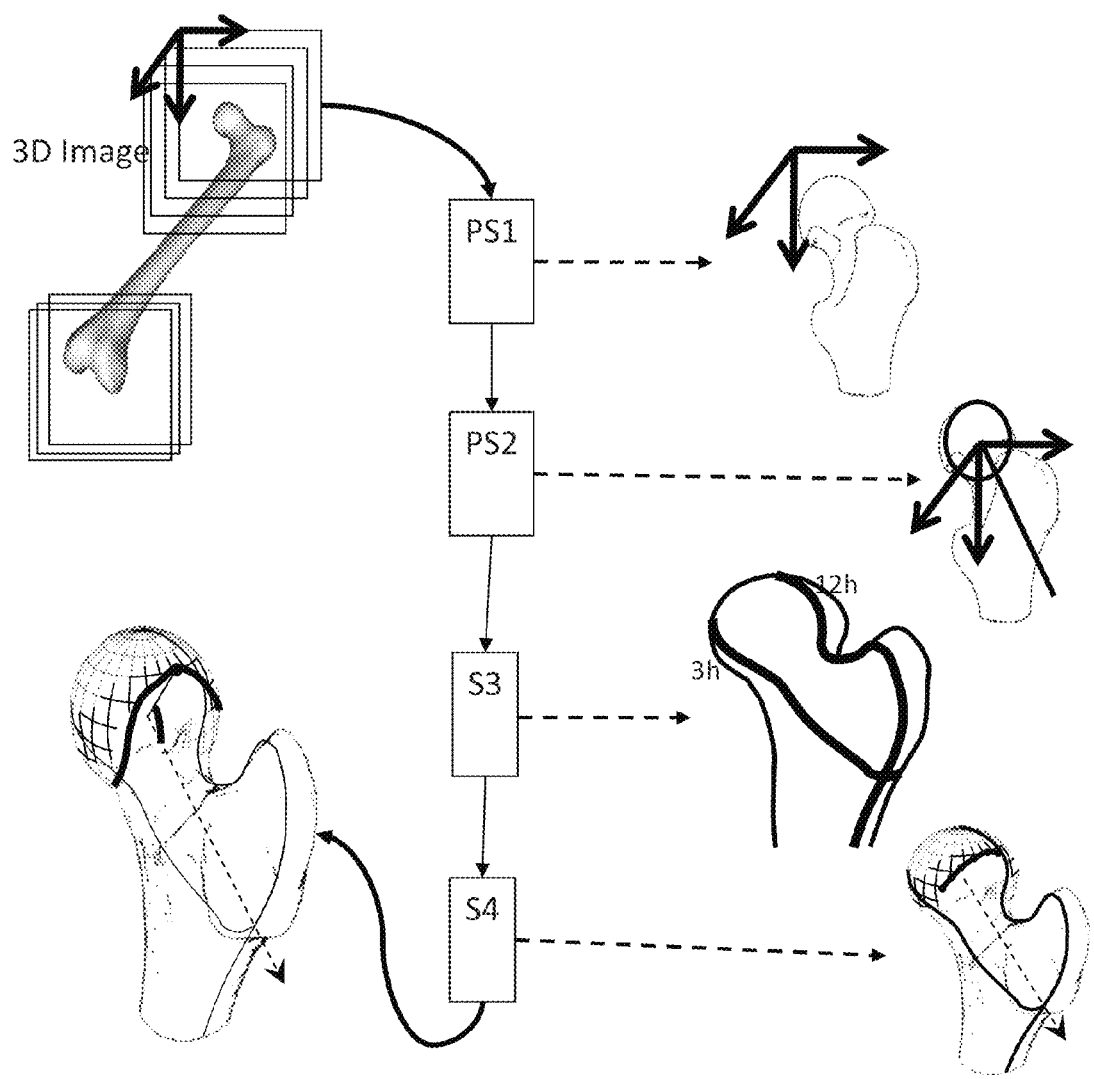
FIG. 1 is a representation of the different steps being performed in the method, illustrating the initial input, the final output and the intermediates results of each step.

As illustrated in FIG. 1, a 3D medical image examination of the patient is performed in order to provide a 3D image of the hip bones using a specific predefined protocol as initial input to the method. As an example of medical image examination, a computer tomography (CT) examination can be performed. In addition to the conventional 3D image acquisition protocol for the hip, our method requires the acquisition of a few extra images at the level of the knee. The 3D image is represented by a stack of parallel 2D images, with known relative positions. The acquisition of the 3D image is a preliminary step that can be directly included in the method of the invention or carried out previously.

The method is implemented as image processing software running on a standard computer. The user can interact with the software by a standard user interface medium like a mouse, touch screen or the like. Images are displayed on the monitor of the computer. At the beginning, the software is used to select and load the 3D image of the specific patient.

As shown in FIG. 1, the method contains successive steps, using as input the 3D image of the bone, and producing as output the indices characterizing the bump deformation of the head-neck junction of the bone. The first two steps PS1 and PS2 are preliminary steps necessary for the method of the invention but they are not in the scope of the invention itself. Therefore the first two steps are not described in full details, but only examples of their implementation and the resulting elements from these steps are described.

Figure 2:
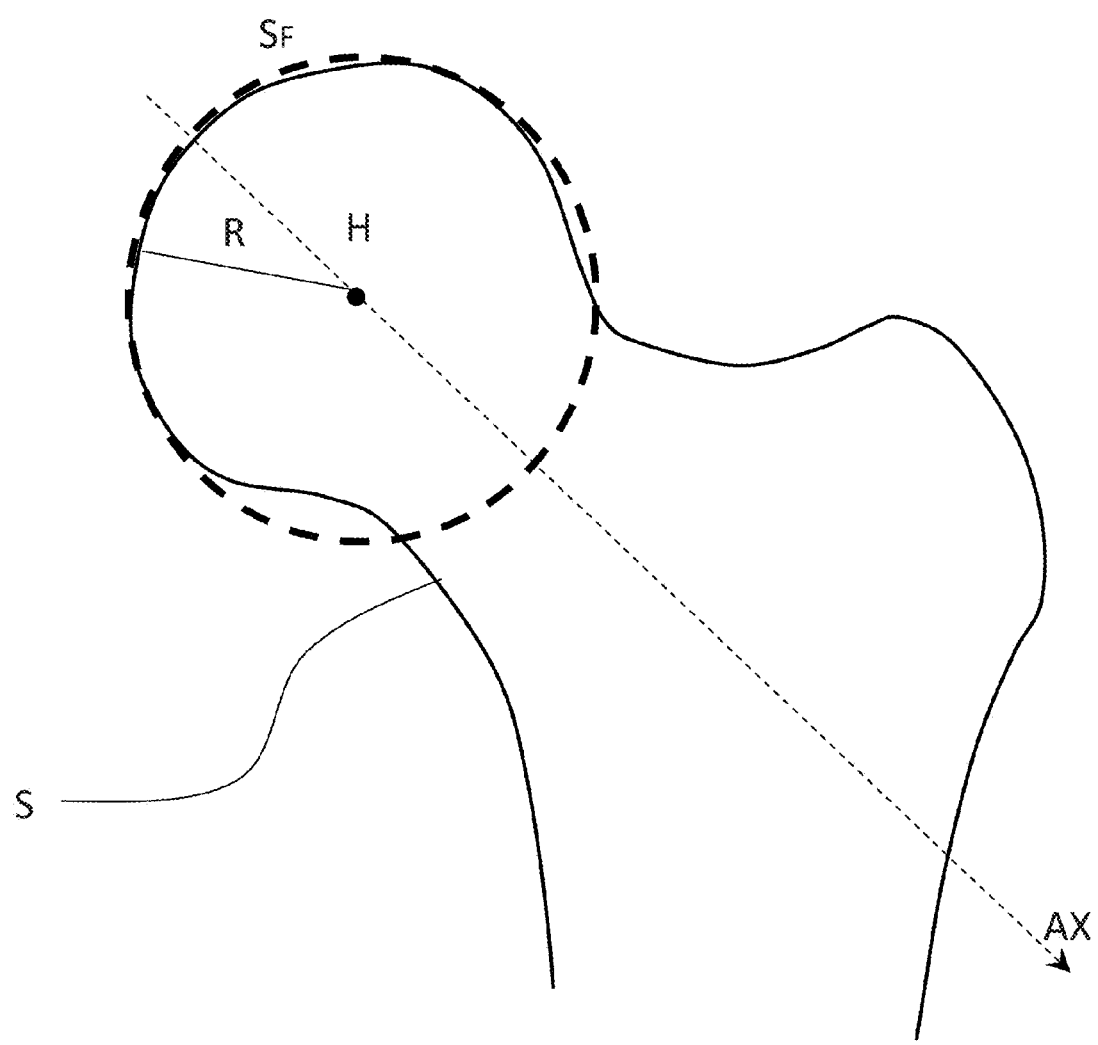
FIG. 2 is a general perspective view of the proximal femur showing the femoral head with a fitted sphere and the neck axis.

The first preliminary step PS1 of the method consists in creating from the 3D medical image of the bone, a 3D surface model of the bone surface S as illustrated in FIG. 2. In the case of CT image, a thresholding process is used to determine an initial surface model by comparing each value of the 3D image point to a predefined threshold value in Hounsfield units representing cortical bone, and retaining points that have a value close to the threshold value, "close" generally meaning within a range of +10% and −10% from the threshold value. It generates multiples binary objects defining connected components in the space of the 3D image. Additional processing using well known mathematical morphology operators is applied to those binary objects to eliminate small connected components and to fill the inside of closed surfaces so that only the external surface of the bone remains. However, the generated surface model S is usually not perfect since the thresholding tends to merge the bone surface with adjacent bones and to create some defects in the surface. Those imperfections are due to many phenomena including the quality of image acquisition and reconstruction, but also to the poor quality of bone density in some pathological areas. Similar conventional methods such as the marching cube or the dividing cube can be applied to build a surface model of the bone. In the following, the surface of the bone reconstructed from the 3D image is referred to as the 3D surface model. The 3D surface model comprises different portions of anatomical surfaces, including the head surface and the neck surface.

The next preliminary step PS2 starts by the identification in the 3D surface model a sphere $S_F$ fitting the spherical portion of the head of the bone as illustrated in FIG. 2. Several methods exists for computing that sphere $S_F$, from fully manual identification of circles in at least two orthogonal 2D reformatted slices selected so as to pass through the head to fully automatic iterative methods, converging to the best fitting sphere, thus providing a 3D head center point H and a radius R.

One example of a method for the determination of the sphere $S_F$ is to apply an iterative method based on the identification of an approximate head center point and an approximate radius, and then applying robust least-square fitting of a sphere to the 3D surface model points, starting from the approximate head center point and the approximate radius. The result is the determination of the head center point H and the radius R of the sphere $S_F$.

Secondly, from the detected head center H, it is necessary to identify the 3D neck axis AX, characterizing the orientation of the neck of the bone. Again, several methods can be applied, from manual identification of lines in at least two orthogonal 2D reformatted slices selected so as to pass through the neck, to fully automatic iterative methods.

Figure 3A:
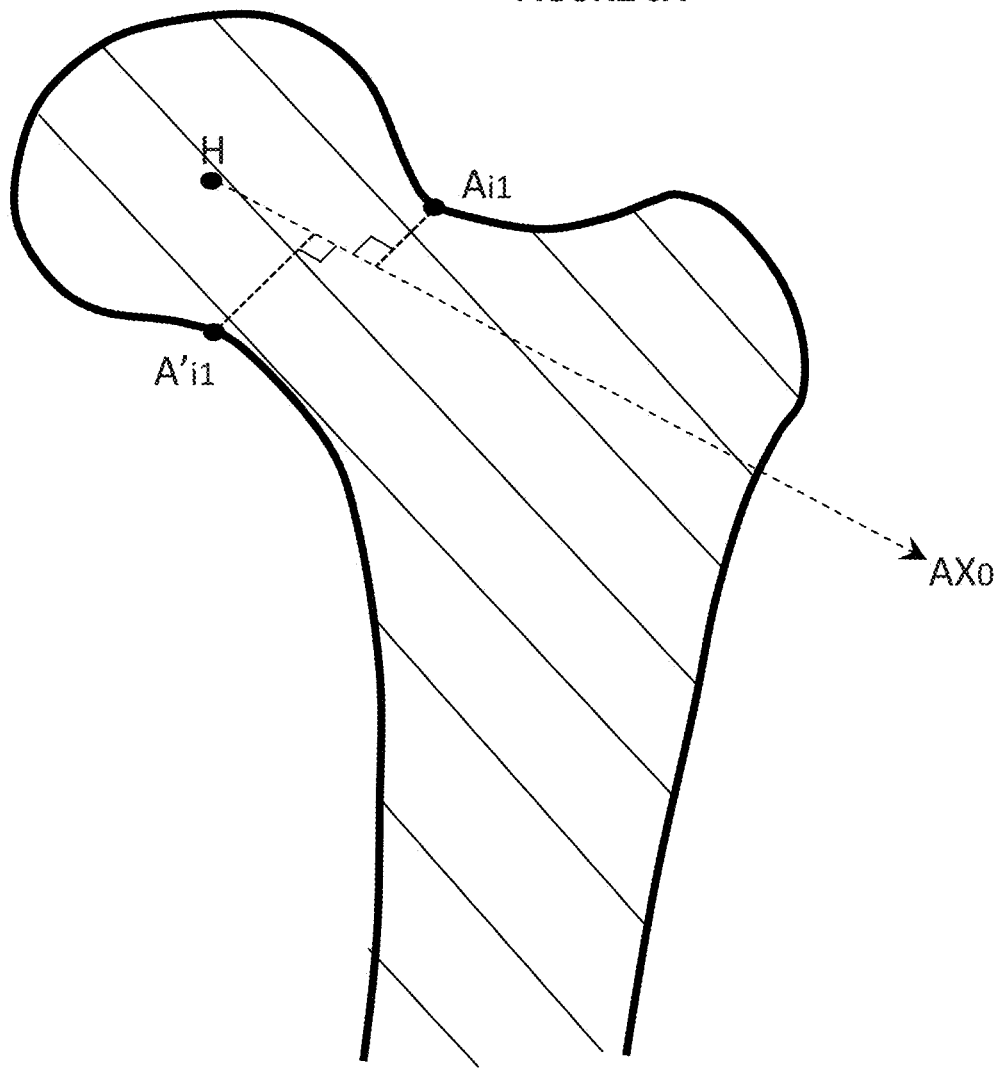
FIGS. 3A and 3B show two orthogonal cross-sectional views of the proximal femur illustrating one method to determine the neck axis.
Figure 3B:
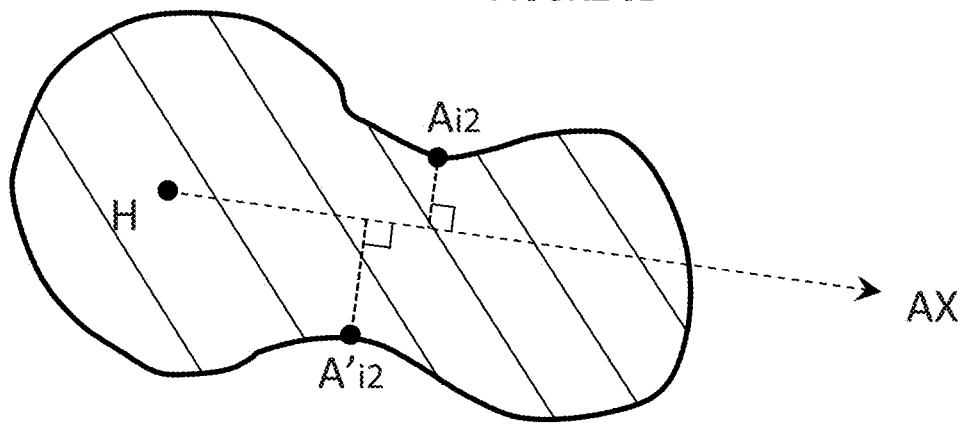

One example of an option for the detection the neck axis AX is illustrated in FIGS. 3A and 3B. It consists in applying an iterative method based on the identification of an approximate axis $AX_0$ passing through the head center H and then applying a minimization process in two orthogonal cross-sections of the 3D surface model passing through $AX_0$. In each section, the process is to adjust the position of $AX_0$ in order to minimize the distances from $AX_0$ to the contours of the neck portion in the cross-section of the 3D surface model. As illustrating in FIGS. 3A and 3B, the closest points $A_i$ and $A_i'$, of the contours of the neck portion on each side of the axis $AX_0$ are computed in both cross-sections. The minimization process consists in adjusting the position of $AX_0$ in both cross-sections in order to minimize the distance of the points $A_i$ and $A_i'$, to their respective orthogonal projection on $AX_0$. The resulting axis is the neck axis AX.

Figure 4A:
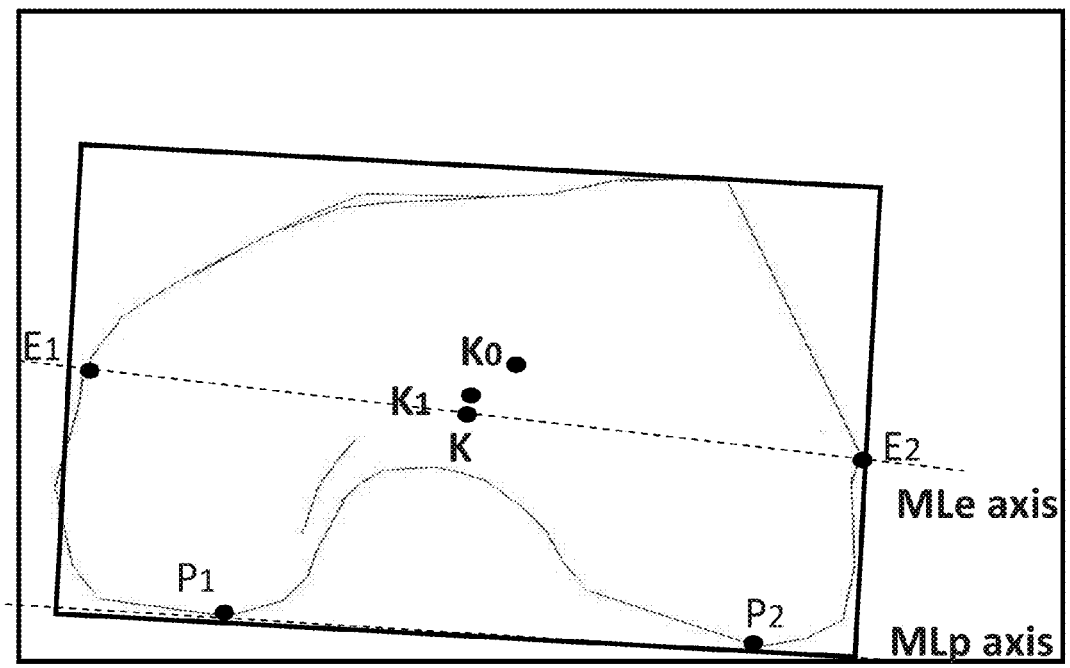
FIG. 4A shows an image of a distal knee slice from the 3D image illustrating the computation of knee reference points and axes.
Figure 4B:
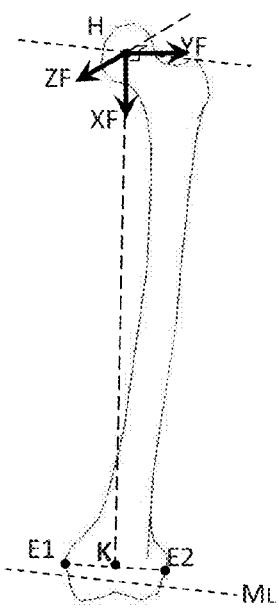
FIG. 4B is a general perspective view of the femur illustrating the construction of the 3D mechanical referential of the femur.

Finally, once the femoral head sphere $S_F$ with its center H and the femoral neck axis AX have been determined, a 3D mechanical femur coordinate system is constructed from the femur head center H, the knee center K and the knee transverse axis ML that joins the points M and L which are the medial and lateral epicondyles of the knee or that joins the most posterior points of the knee condyles. These last two anatomical elements are determined from 3D images acquired at the level of the knee joint as shown in FIG. 4A. From these images, the knee center point K is determined. It is easy to find the centroid of these images after appropriate thresholding and compute an initial knee center K0. From that point, a rectangular box is computed around K0 in the axial image plane containing K0, such box being adjusted to be the smallest in contact with surface points detected on the bone. The center of the rectangular box becomes the estimation of the knee center K1. To refine even more the location of the knee center, it is further possible to extract the femur Medio-Lateral axis MLe as being the epicondylar axis in the knee 3D image. The epicondyles points E1 and E2 can be automatically detected by searching for example the two most distant bone points in the rectangular box computed above, passing within a given range of the knee center point K1. Other algorithms can be used to detect the epicondylar axis. Once this MLe axis has been determined, the knee center point K can be defined as the middle of the MLe segment. In another embodiment, a Medio-Lateral axis that we can extract is the postero-condylar axis MLp. It can be extracted using iterative methods to search for the most posterior points in the axial images of the knee.

From all these anatomical elements, the femur coordinate system is constructed as follows: its origin is centered on the femoral head center H, the $X_F$ axis is defined by the vector HK, the $Z_F$ axis is defined as the vector product of $X_F$ by ML, and the $Y_F$ axis is defined as the vector product of $Z_F$ by $X_F$. It is then possible to measure the neck version angle, which is the neck axis orientation relatively to the ML axis in the axial plane of the femur coordinate system, which is an important element to be taken into account in the analysis of the whole case for decision of the surgical treatment.

It is possible to use directly the 3D image referential to orientate the 3D mechanical referential, though assuming the position of the patient during the exam can be controlled to meet expected mechanical orientation. In further description, the anatomical directions are defined from the axes of the 3D mechanical referential and of the neck as follows:

[A] Superior-inferior direction is orientated along $X_F$,
[B] Medial-lateral direction is orientated along $Y_F$,
[C] Posterior-anterior direction is orientated along $Z_F$,
[D] And Proximal-distal direction is orientated along the neck axis, in the direction from the head center H down to the neck.

The next step S3 of the method consists in mapping automatically on the 3D surface model of the head of the bone, a clock face referential system, which has clinical significance when addressing bones with a head portion.

Figure 5A:
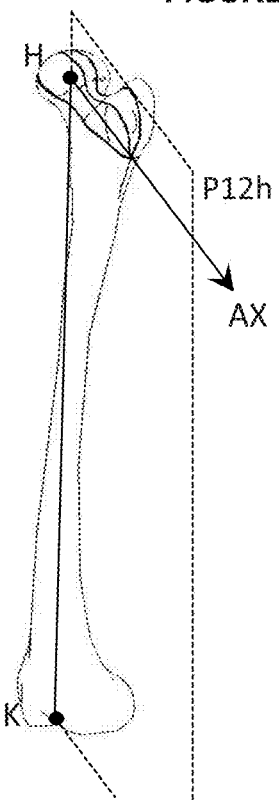
FIGS. 5A and 5B are perspective views of the femur illustrating the construction of the clock face referential from radial planes rotating around the neck axis.
Figure 5B:
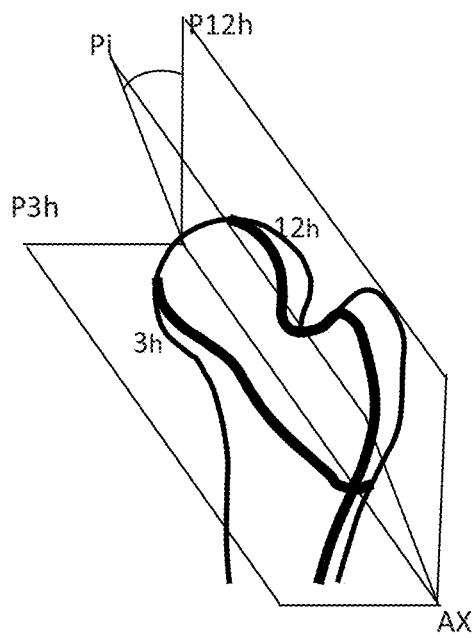

As shown in FIGS. 5A and 5B, the clock face is a radial referential system representing 12 hours angular segments commonly used by surgeons to identify location of points on the femoral head surface. The clock face can be fully determined by determining the location of the 12 o'clock plane $P12h$. Successive rotations of this plane around the neck axis AX will then define the 1 o'clock, 2 o'clock, and followings, until 11 o'clock location. As shown in FIG. 5A, our method consists in determining the position of the 12 o'clock plane $P_{12h}$, as the location of the most superior portion of the intersection line of the 3D surface model and the plane passing through the neck axis AX and the knee center point K determined by the method defined previously. It provides a fully automated determination of the clock face from the 3D image.

Once the clock face has been determined on the femur, the goal is to characterize the femur bump deformation by superimposing the 3D femoral head sphere $S_F$ and the femur 3D bone surface model in order to locate and quantify the 3D curve where the two surfaces intersect.

The next step S4 of the method consists in determining automatically the 3D curve characterizing the head-neck junction of the bone. To determine the 3D head-neck junction curve, series of hemi-planes Pi passing through the head center H and around the neck axis AX are computed in the 3D image volume, as shown in FIG. 5B. Those hemi-planes Pi are identified by a clock index i, starting at 12 o'clock. In a preferred embodiment, hemi-planes Pi are computed every hour around the clock. But it could be also every half hour or even more precisely. One of the difficulty of this step is that the 3D surface model of the head neck junction represents an imperfect surface, and local small deviations generated by artifacts during the surface reconstruction can lead to an erroneous determination of the 3D curve.

Figure 6:
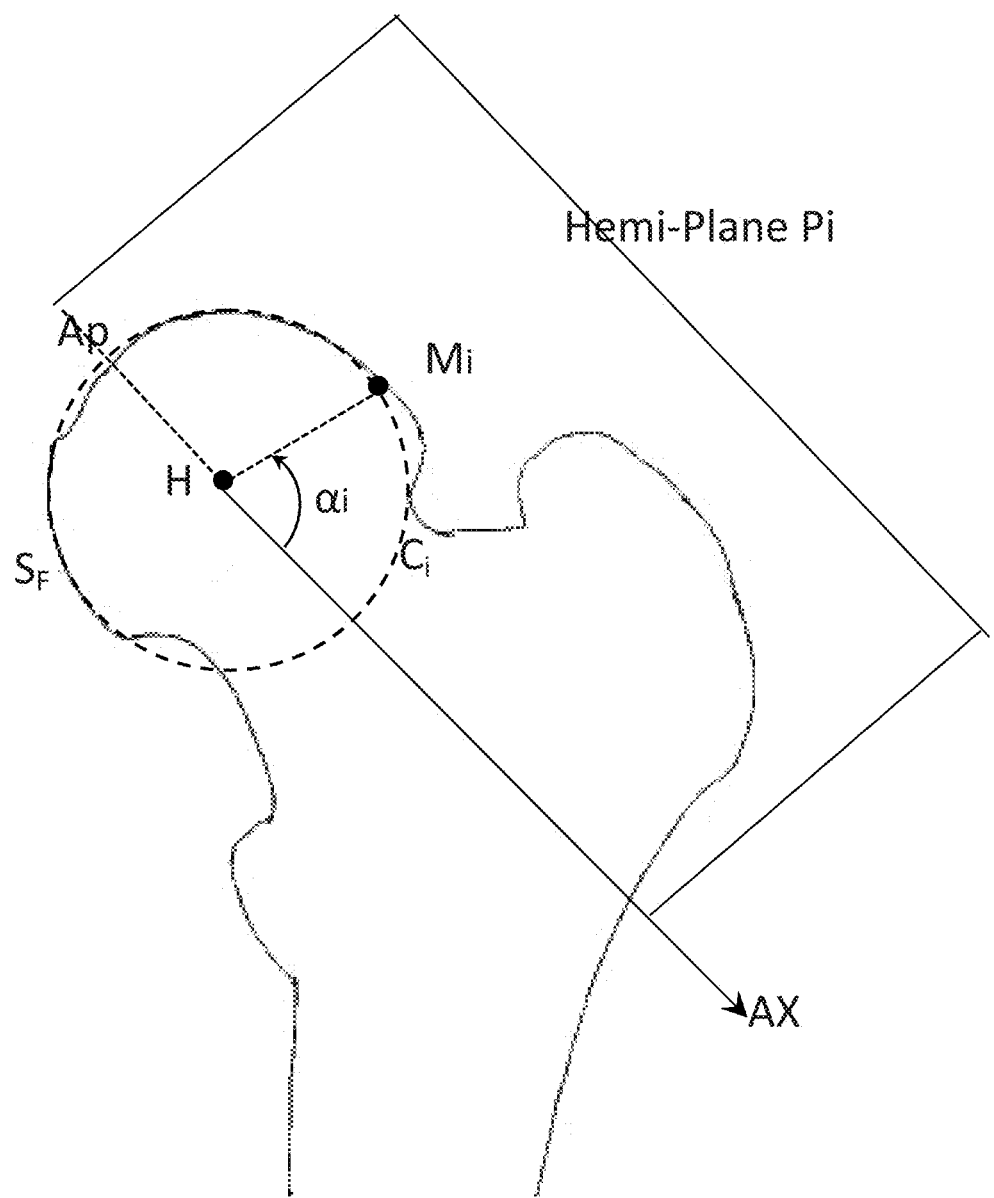
FIG. 6 shows a cross-sectional view of the proximal femur computed from one radial plane along the neck axis, illustrating the detection of head-neck junction point.

As shown on FIG. 6, for each plane hemi-plane Pi around the neck axis AX, for all indexes i in the clock face (i=12, 1, 2, . . . 11), the intersection of the femoral head sphere $S_F$ with the hemi-plane Pi is computed producing a circle Ci overlaying the intersection of the 3D surface model with the hemi-plane Pi producing a contour of the femoral head FCi. Now for each hemi-plane Pi, a point Mi on the contour FCi corresponding to the location where the contour FCi deviates outside of the circle Ci is computed according to the following description:

A femoral head apex point Ap is defined as the intersection point between the femoral neck axis AX and the circle Ci opposite to the neck.

The point Mi is determined in the following manner: the closest point from the femoral head apex Ap which is lying on the contour FCi and which is lying outside the circle Ci, over a given threshold distance TD, and which neighbour M'i further down along the contour FCi in the direction of the neck is also lying outside the circle Ci. Such a threshold distance TD is generally set between 0.5 mm and 1 mm and it must be below 2 mm to provide accurate results. The neighbour M'i along the contour FCi is generally considered up to a maximum distance of 2 mm for Mi. This point Mi is considered as the head-neck junction point of the bone in the hemi-plane Pi.

Figure 7:
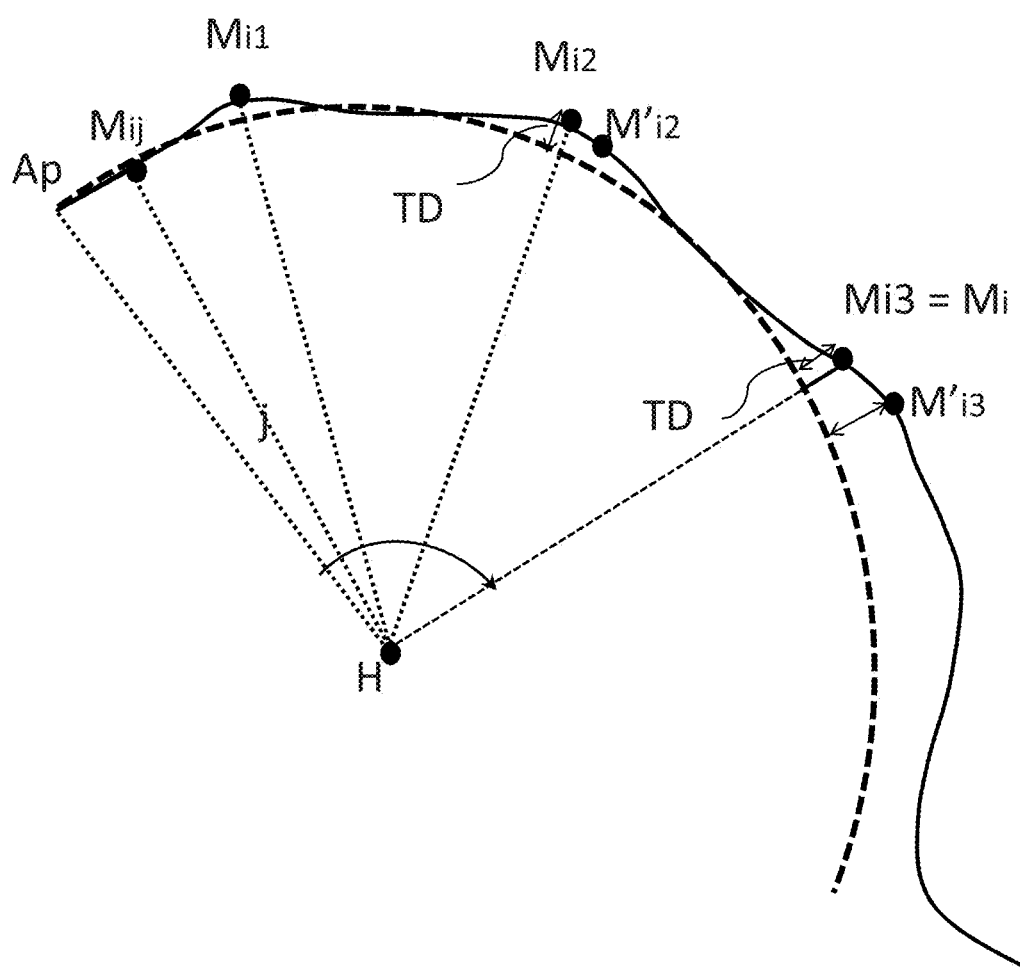
FIG. 7 shows a zoom-in cross-sectional view of the proximal femur computed from one radial plane along the neck axis, illustrating the detection of head-neck junction point using a threshold value when irregularities are present on the 3D surface model.

In one embodiment of the method, the process for detecting the point Mi complying with the above conditions is illustrated in FIG. 7 and is carried out automatically in the following manner:

Starting from the apex point Ap, a point Mij (wherein j is an integer greater than 1 of an index position of an angle between 0° and 180° is following the contour of the femoral head in the direction of the neck. If a first point Mi1 lying outside the circle Ci is detected. However, if its distance from the border of the circle Ci is smaller than the threshold distance TD, Mi1 is discarded and the point Mij continues its path on the femoral head contour in the direction of the neck. If a next point Mi2 lying outside the circle Ci is detected, which distance from the border of the circle Ci is equal to or greater than the threshold distance TD, then its neighbour M'i2 on the contour of the femoral head in the direction of the neck is also tested. If M'i2 is lying outside the circle Ci but its distance from the border of the circle Ci is smaller than the threshold distance, then Mi2 is also discarded and the point Mij continues its path on the femoral head contour in the direction of the neck. If a next point Mi3 lying outside the circle Ci is detected, which distance from the border of the circle Ci is equal or greater than the threshold distance TD, then its neighbour M'i3 on the contour of the femoral head in the direction of the neck is also tested. If M'i3 is lying outside the circle Ci at a distance from the border of the circle Ci greater than the threshold distance TD, then the point Mi3 is selected to be the point Mi searched for.

This process avoids detecting small local bumps which might come from the imperfection of the reconstructed 3D surface model, and insures to take into account only the actual bump of the head-neck deformation when determining the 3D curve of the head-neck junction.

In another embodiment of the method, the neighbour test described previously can also be performed in the orthogonal direction to the hemi-plane Pi, the neighbours being then located on the 3D surface model, on both sides of the contour FCi, thus reinforcing criteria for the detection of an actual bump in 3D and not only in 2D.

In another embodiment of the method, the position of the detected point Mi in the hemi-plane Pi on the contour FCi can be further adjusted in order to comply with a continuity constraint with point Mi+1 and point Mi−1 respectively detected on the contours FCi+1 and FCi−1 in the hemi-planes Pi+1 and Pi−1.

In order to anticipate on the smoothness of the final 3D curve created from all Mi points, it is possible to adjust the position of the central point Mi in a triplet of contiguous points (Mi−1, Mi, Mi+1) for all points Mi, by minimizing the sum SMi of the distances from Mi−1 to Mi, and Mi to Mi+1. The point Mi is therefore adjusted into the point Ni, where Ni is lying on the contour FCi, outside the circle Ci, within a distance less or equal to the threshold TD and such that the sum SNi of the distances from Mi−1 to Ni, and Ni to Mi+1 is smaller than SMi.

Figure 8:
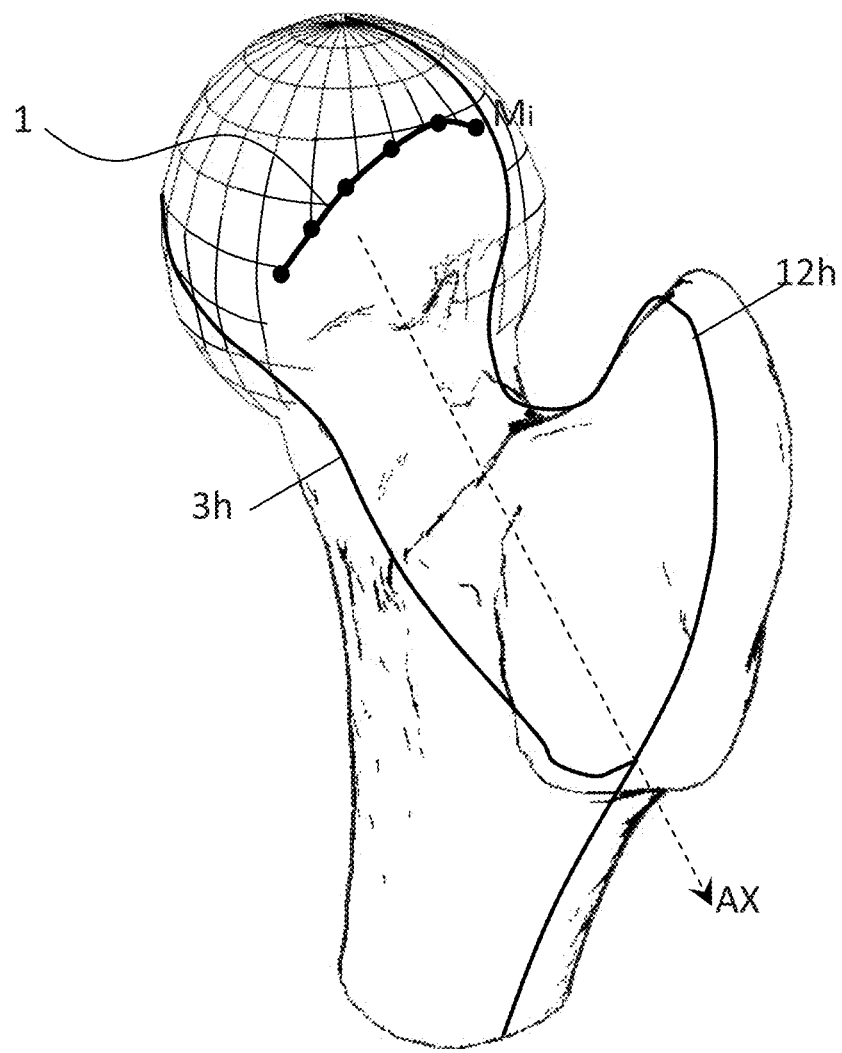
FIG. 8 is a perspective view of the femur showing the minimum 3D curve of the head-neck junction constructed from contiguous junction points.

As shown in FIG. 8, when all the points Mi have been determined in the successive Pi hemi-planes around the clock, linking all points Mi around the femoral head surface determines a 3D curve 1.

In one embodiment of the method, the linking of the points Mi can be performed using straight linking segments between contiguous points Mi, thus creating a 3D pecked line.

In another embodiment, a minimal 3D curve can be determined by fitting a 3D spline curve of minimal length, interpolating contiguous Mi points.

Now in each hemi-plane Pi, the 2D alpha angle $\alpha i$ which is a common index used for characterizing the femoral head-neck junction is automatically computed as the angle between the hemi-line from the femoral sphere center H and in the direction of the neck axis AX and the hemi-line from femoral sphere center H and the point Mi as shown in FIG. 6. The 3D curve passing through the Mi points is then referred to as the 3D alpha curve.

Figure 9:
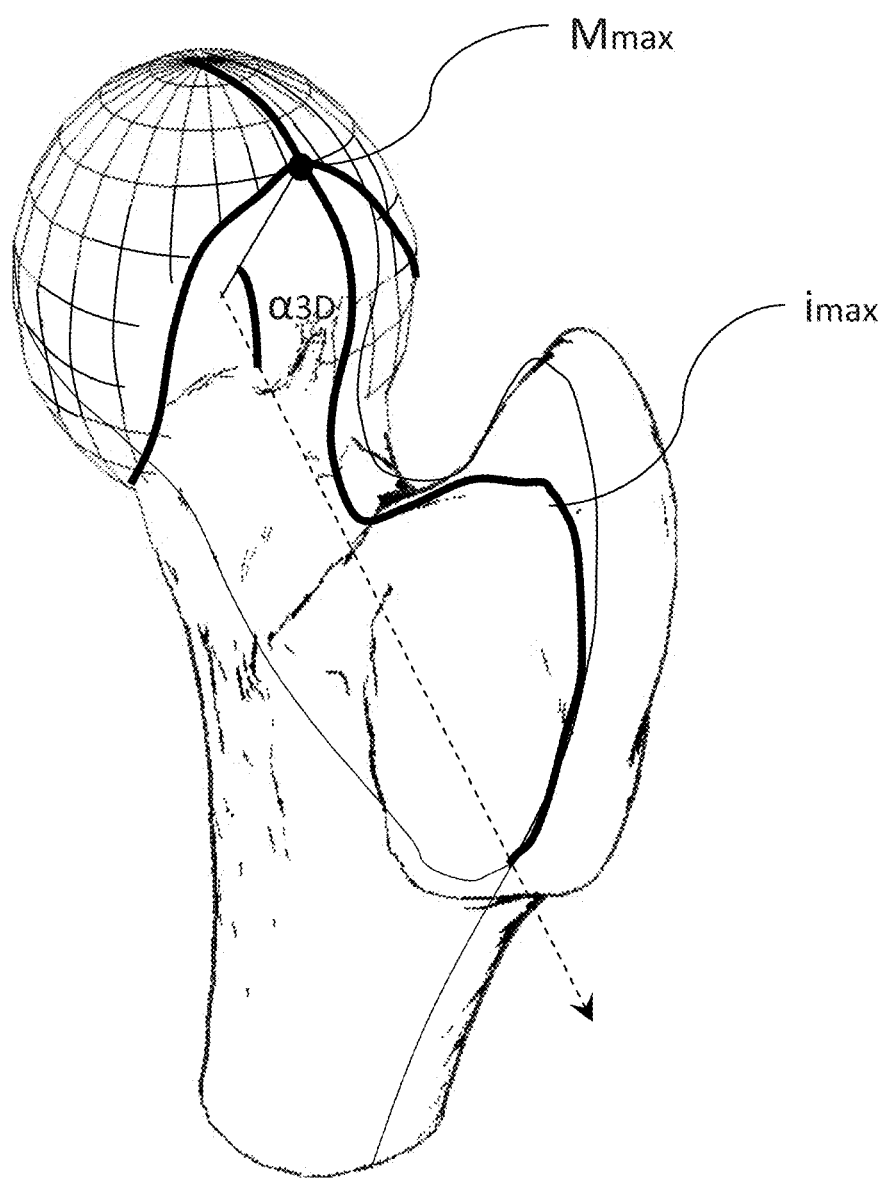
FIG. 9 is a perspective view of the femur showing the summit point of the 3D curve of the head-neck junction and the determination of the bump characteristic indices.

As illustrated in FIG. 9, and as a synthesis from the steps described above, from all the 2D alpha angles $\alpha i$, a 3D alpha angle $\alpha 3D$ is determined as the maximum value amongst the 2D alpha angles $\alpha i$. The corresponding point Mi determines the summit of the head-neck junction curve characterizing the bump deformation and is referred to as the maximum point Mmax and the corresponding clock index as the maximum index iMax.

The maximum $\alpha 3D$ angle is a first parameter that characterizes the 3D bump by quantifying the "amount" of the bone deformity. The maximum clock index iMax is a second parameter that characterizes the 3D bump by giving its location on the clock face. The 3D alpha curve and the pair of indices ($\alpha 3D$, iMax) then fully characterize the femoral head-neck junction bump deformation. Together with the neck version measurement described previously, the parameters characterizing the bump will enable the surgeon to decide of the most appropriate surgical treatment.

Advantages

The advantage of the invention is the precise, and automatic determination of characteristic elements quantifying and locating the deformation of the nead-neck junction of a bone in a 3D image requiring the least possible input from user interaction. From the determination of these elements, it is then possible for surgeons to decide on the most appropriate surgical treatment. Usually those characterization measurements are performed manually by a radiologist, which takes time and efforts and is prone to human errors or inaccurate measurements, and potentially misleading the choice of surgical treatment. Our method provides then a fast and more reliable process to perform these measurements during the analysis of the pathology.

The invention claimed is:

1. A method for automatically determining, on a bone comprising a head portion contiguous to a neck portion, parameters for characterizing a bump deformation on the head-neck junction of the bone from acquired 3D medical image, said method comprising the following steps:
   i) constructing a 3D surface model of the bone from acquired 3D medical image;
   ii) fitting a sphere on the spherical portion of the head of the bone;
   iii) determining a neck axis characterizing the neck portion of the bone;
   iv) determining from the fitted sphere and the neck axis, a clock face referential on the head of the bone rotating around the neck axis;
   v) determining a 3D curve on the 3D surface model characterizing the head-neck junction of the bone;
   vi) determining, from the 3D curve, the summit of the bump deformation of the head-neck junction of the bone, said summit being the point on the 3D curve closest to the apex point of the head of the bone in the direction of the neck axis;
   vii) determining, from said summit of the bump deformation, first and a second parameters characterizing the maximum bump deformation of the head-neck junction of the bone, wherein the first parameter ($\alpha 3D$) is the angle between the hemi-line issued from the center of the fitted sphere in the neck axis direction and the segment joining the center of the fitted sphere and the summit of the bump deformation, and the second parameter (iMax) is a clock index locating on the clock face referential the summit of the bump deformation.

2. The method of claim 1 wherein the step of determining the clock face referential is performed by an automatic computation comprising of the following steps:
   i) determining a 12 o'clock superior coronal hemi-plane passing through the neck axis of the bone;
   ii) determining on the head of the bone the 12 o'clock index at the location of the intersection of the coronal hemi-plane and the 3D surface model of the bone, at the most superior portion of the head of the bone;
   iii) determining on the head of the bone the successive clock indices by rotating the coronal hemi-plane around the neck axis for each hour, the current hour index being determined at the location of the intersection of the current rotated hemi-plane and the 3D surface model of the bone.

3. The method of claim 2 wherein said 12 o'clock superior coronal hemi-plane is determined from a superior portion of a coronal plane containing the neck axis and passing through a knee center point defined from the knee 3D image from and which with the the center of the fitted sphere determines the 3D mechanical vertical axis; the superior portion of the coronal plane being the hemi-plane starting at the level of the neck axis and extending in the opposite direction from the knee center point.

4. The method of claim 1, wherein the step of determining the 3D curve is performed by an automatic computation comprising the following steps:
   i) determining a set of radial hemi-planes containing the neck axis and rotating around neck axis on the clock face referential;
   ii) determining for each radial hemi-plane a point issued from the apex of the fitted sphere and moving in the direction of the neck along a head contour curve determined from the intersection of the 3D surface model and the radial hemi-plane;
   iii) determining the first position of the point moving along the head contour curve where it is lying outside a circle determined by the intersection of the fitted sphere and the radial hemi-plane, over a predefined threshold distance from the contour of the circle; said point defining a head-neck junction limit point;
   iv) determining from all radial hemi-planes a set of 3D head-neck junction limit points;
   v) determining a 3D curve on the 3D surface model of the bone as an optimal 3D curve passing through the set of 3D intersecting points; said 3D curve defining the 3D head-neck junction curve.

5. The method of claim 4 wherein the radial hemi-planes are determined at regular angular intervals, at least for every hour around the clock face referential.

6. The method of claim 4 wherein the predefined threshold is in an interval of minimum 0.5 mm and maximum 2 mm.

7. The method of claim 4, wherein the determination of a head-neck junction limit point in one radial hemi-plane further complies with the condition that its neighbor points within a maximum distance of 2 mm further down along the head contour curve in the direction of the neck are also lying outside the circle over the threshold distance.

8. The method of claim 7 wherein the determination of each head-neck junction limit point in all radial hemi-planes further comprises an adjustment of their position within the threshold limit, along their respective head contour curve so to minimize the relative 3D distance of contiguous pairs of point in contiguous triplets of 3D head-neck junction limit points.

9. The method of claim 4 wherein said optimal curve is determined by a 3D pecked line joining contiguous points in the set of 3D head-neck junction limit points.

10. The method of claim 4 wherein said optimal curve is determined by a 3D spline curve of minimal length interpolating the contiguous points in the set of 3D head-neck junction limit points.

11. The method of claim 10 wherein the points in the set of 3D head-neck junction limit points are further adjusted along their respective femoral head contours, while still lying outside the fitted sphere contour within the limit of the predefined threshold distance, so as to produce a smooth slope of the 3D head junction curve at the location of each 3D head-neck junction limit point.

12. A system for determining, on a bone comprising a head portion contiguous to a neck portion, parameters for characterizing a bump deformation on the head-neck junction of the bone from acquired 3D medical image, the system comprising a computer including a memory and a processing unit adapted to run a computer program, wherein said computer program comprises at least one algorithm applying the method of claim 1.

* * * * *